United States Patent
Yamamoto

(10) Patent No.: US 8,062,591 B2
(45) Date of Patent: Nov. 22, 2011

(54) CLINICAL LABORATORY TEST APPARATUS AND CLINICAL LABORATORY TEST SYSTEM

(75) Inventor: Norimasa Yamamoto, Kobe (JP)

(73) Assignee: Sysmex Corporation, Kobe (JP)

( * ) Notice: Subject to any disclaimer, the term of this patent is extended or adjusted under 35 U.S.C. 154(b) by 568 days.

(21) Appl. No.: 10/949,099

(22) Filed: Sep. 24, 2004

(65) Prior Publication Data

US 2005/0070019 A1    Mar. 31, 2005

(30) Foreign Application Priority Data

Sep. 29, 2003 (JP) ................. 2003-337273

(51) Int. Cl.
*G01N 21/00* (2006.01)
*G01N 33/48* (2006.01)

(52) U.S. Cl. .......... 422/63; 422/64; 422/65; 422/68.1; 436/43; 436/47; 436/48; 436/63; 435/13; 435/286.1

(58) Field of Classification Search .......... 422/63, 422/64, 65, 68; 436/43, 47, 48, 63; 435/286.1, 435/13; 702/31

See application file for complete search history.

(56) References Cited

U.S. PATENT DOCUMENTS

| | | | |
|---|---|---|---|
| 5,470,534 A * | 11/1995 | Imai et al. ............... | 422/67 |
| 5,988,857 A | 11/1999 | Ozawa et al. | |
| 6,019,945 A * | 2/2000 | Ohishi et al. ............. | 422/65 |
| 6,106,778 A * | 8/2000 | Oku et al. ............... | 422/50 |
| 7,390,677 B2 | 6/2008 | Nakashima et al. | |
| 2002/0025064 A1 | 2/2002 | Itoh | |
| 2002/0055176 A1 * | 5/2002 | Ray ........................ | 436/67 |
| 2003/0070498 A1 * | 4/2003 | Ohyama et al. ........ | 73/863.01 |
| 2003/0082662 A1 * | 5/2003 | Nakashima et al. .... | 435/13 |
| 2004/0018629 A1 * | 1/2004 | Kawate .................. | 436/63 |

FOREIGN PATENT DOCUMENTS

| | | |
|---|---|---|
| JP | 05-307042 | 11/1993 |
| JP | 06-102272 | 4/1994 |
| JP | 06-265554 | 9/1994 |
| JP | 07-280814 | 10/1995 |
| JP | 08-114600 | 5/1996 |
| JP | 10-048214 | 2/1998 |
| JP | 10-62426 | 3/1998 |
| JP | 11-101798 | 4/1999 |
| JP | 11-295305 | 10/1999 |
| JP | 2002-5942 | 1/2002 |
| WO | WO 01/96868 | 12/2001 |

* cited by examiner

*Primary Examiner* — Jill Warden
*Assistant Examiner* — Dean Kwak
(74) *Attorney, Agent, or Firm* — Brinks Hofer Gilson & Lione

(57) ABSTRACT

The clinical laboratory test apparatus includes: an analyzing unit for analyzing a specimen; a reception part for receiving specimen information before analysis of the specimen; a discrimination part for discriminating whether or not a specimen is suited for analysis based on the specimen information; and a control part for controlling the analyzing unit based on the discrimination result obtained by the discrimination part.

12 Claims, 14 Drawing Sheets

Fig.5

| Item | Threshold value | Anomaly determination equation | Anomaly value |
|---|---|---|---|
| Erythrocyte count | 6.25 million/$\mu$l | >6.25 million/$\mu$l | High erythrocyte count |
| Hematocrit | 70% | >70% | High hematocrit |
| Platelet count | 0.5 million/$\mu$l | >0.5 million/$\mu$l | High platelet count |
| MCV | 120fL | >120fL | High MCV |
|  | 70fL | <70fL | Low MCV |

301 302 303 304

| ID No. | Determination result |
|--------|---------------------|
| 00102348 | Whole blood immunoassay: OK |
| 00230312 | Whole blood immunoassay: OK |
| 00212054 | Whole blood immunoassay: NO |
| 00304191 | Whole blood immunoassay: NO |
| 00300127 | Whole blood immunoassay: OK |

Fig.17

| ID No. | Erythrocyte count | Hematocrit | Platelet count | MCV |
|---|---|---|---|---|
| 00216534 | 530 | 45 | 30 | 85 |
| 00392671 | 270 | 15 | 5 | 67 |
| 00169812 | 390 | 31 | 12 | 79 |
| ⋮ | ⋮ | ⋮ | ⋮ | ⋮ |

US 8,062,591 B2

1

CLINICAL LABORATORY TEST APPARATUS AND CLINICAL LABORATORY TEST SYSTEM

This application claims priority under 35 U.S.C. §119 to Japanese Patent Application No. 2003-337273 filed Sep. 29, 2003, the entire content of which is hereby incorporated by reference.

FIELD OF THE INVENTION

The present invention relates to a clinical laboratory test apparatus and clinical laboratory test system capable of recognizing beforehand whether or not an accurate assay result can be obtained before the specimen is analyzed.

BACKGROUND

An immunoassay method is known which corrects the amount (assay value) of antibody or antigen in blood obtained by immunoassay of a whole blood specimen based on a hematocrit value obtained from a blood analyzer, so as to obtain the amount of antibody or antigen (corrected value) in the serum or plasma (refer to Japanese Laid-Open Patent Publication No. 10-48214).

In this method, when the specimen has an abnormally low hematocrit value, a problem arises inasmuch as an accurate correction value (amount of antibody or antigen in the serum or plasma of the specimen) cannot be obtained.

SUMMARY

In view of the above information, an object of the present invention is to provide a clinical laboratory test apparatus and clinical laboratory test system capable of recognizing that a specimen is unsuitable for assay before the assay of the specimen for which an accurate assay result cannot be obtained.

The clinical laboratory test apparatus of a first aspect of the present invention includes: (a) an analyzing unit for analyzing a specimen; (b) a reception means for receiving specimen information before analysis of the specimen; (c) a discrimination means for discriminating whether or not a specimen is suited for analysis based on the specimen information; and (d) a control means for controlling the analyzing unit based on the discrimination result obtained by the discrimination means.

The clinical laboratory test system of a second aspect of the present invention includes: (a) a first specimen analyzing part for analyzing a specimen; (b) a second analyzing part for analyzing a specimen; and (c) an information transmission means for transmitting specimen information obtained by the first specimen analyzing part to the second specimen analyzing part; wherein the second specimen analyzing part is provided with an analyzing unit for analyzing a specimen; a discrimination means for discriminating whether or not a specimen is suited for analysis before the specimen is examined based on specimen information transmitted by the information transmission means; and a control means for controlling the analyzing unit based on the discrimination result of the discrimination means.

The clinical laboratory test system of a third aspect of the present invention includes: (a) a first specimen analyzing part for analyzing specimens; (b) a second analyzing part for analyzing specimens; and (c) an information transmission means for transmitting specimen information between the first specimen analyzing part and the second specimen analyzing part; wherein the information transmission means

2 comprises a discrimination means for discriminating whether or not a specimen is suited for analysis by the second specimen analyzing part based on the analysis information obtained when the specimen was analyzed by the first specimen analyzing part; and the discrimination result of the discrimination means is transmitted to the second specimen analyzing part; and wherein the second specimen analyzing part comprises an analyzing unit for analyzing specimen; and a control means for controlling the analyzing unit based on the discrimination result transmitted from the information transmitting means.

The clinical laboratory test system of a fourth aspect of the present invention includes: (a) a transport part for transporting containers accommodating specimens; (b) a first specimen analyzing part comprising a first analyzing unit for analyzing specimens accommodated in the containers transported by the transport unit; (c) a second specimen analyzing part comprising a second analyzing unit for analyzing specimens accommodated in the containers transported by the transporting part which have been analyzed by the first specimen analyzing part; and (d) a control means for controlling the transport part, first specimen analyzing part, and second specimen analyzing part; wherein the control means discriminates whether or not a specimen is suited for analyzing by the second specimen analyzing part based on the analysis information obtained when the first specimen analyzing part analyzed the specimen.

The specimen clinical laboratory test method of a fifth aspect of the present invention includes: the steps of receiving specimen information before analysis of a specimen; discriminating whether or not a specimen is suited for analysis based on the specimen information; and determining whether or not to automatically execute analysis of a specimen will be based on the discrimination result.

BRIEF DESCRIPTION OF THE DRAWINGS

FIG. 5 is a table for anomaly determination;
FIG. 17 shows the memory structure of the control part of the whole blood immunoassay apparatus.

DETAILED DESCRIPTION

The embodiments of the present invention are described hereinafter with reference to the drawings. In the following embodiments, a whole blood immunoassay apparatus is described in the examples as an example of the clinical laboratory test apparatus of the present invention.

First Embodiment

Figure 1:
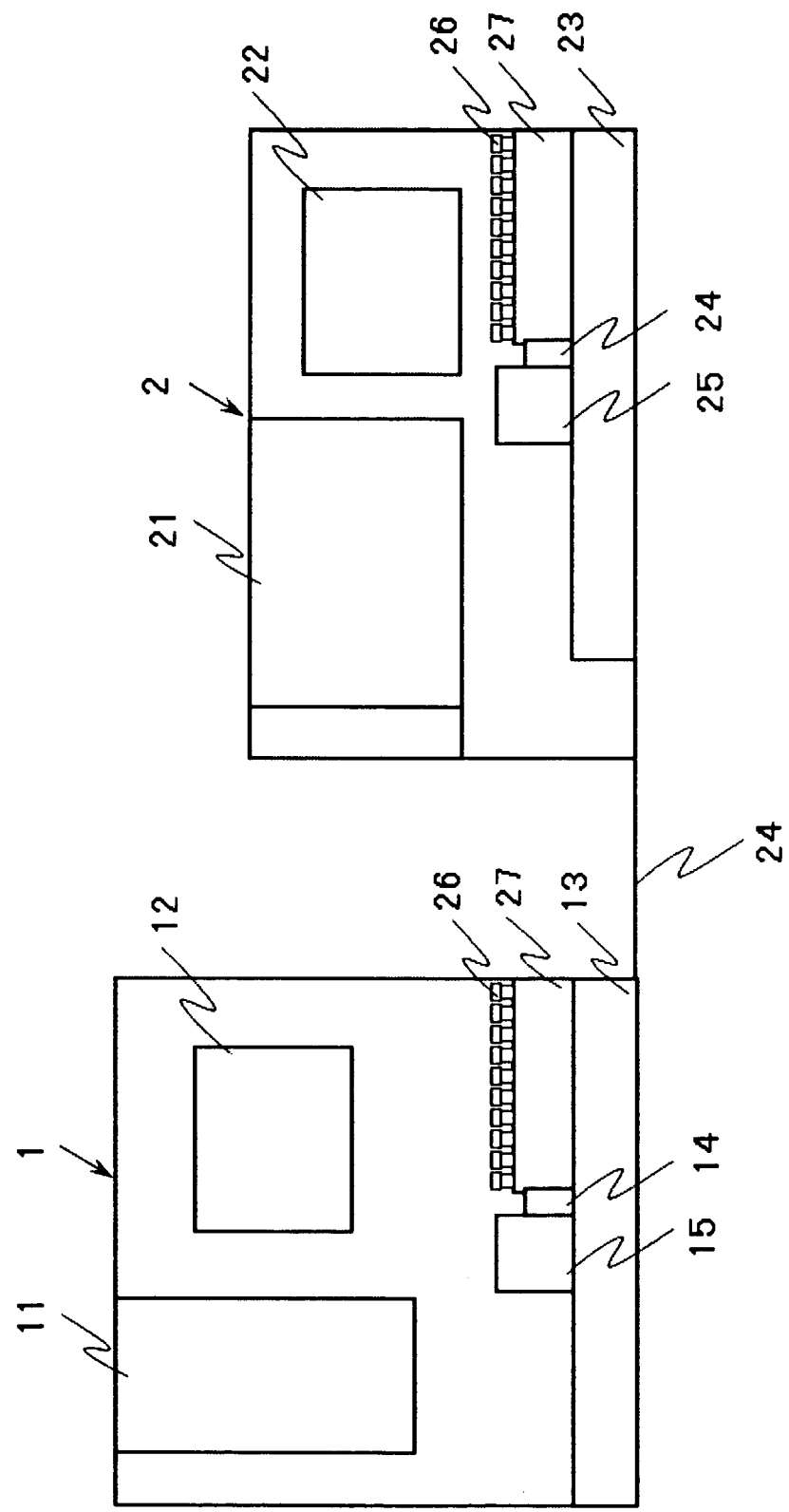
FIG. 1 an exterior view of a first embodiment of the system.

FIG. 1 is an external view showing a first embodiment of the system including a whole blood immunoassay apparatus. The system connects a blood analyzer 1 and whole blood immunoassay apparatus 2 via a communication cable 24 so as to allow communication. The communication cable 24 is an RS232C serial cable.

As shown in FIG. 1, the blood analyzer 1 includes a rack supply unit 13 for supplying one by one a plurality of racks 27 holding sample containers 26, barcode reader 14 for reading the barcode of the sample container 26, sample mixing/suctioning apparatus 15 for mixing and suctioning blood samples of the sample container 26, sample analyzer 11 for analyzing suctioned blood samples, and display/operation unit 12 for inputting analysis conditions and outputting assay results. The display/operation unit 12 is a touch panel-type display capable of display and operation (input).

Figure 2:
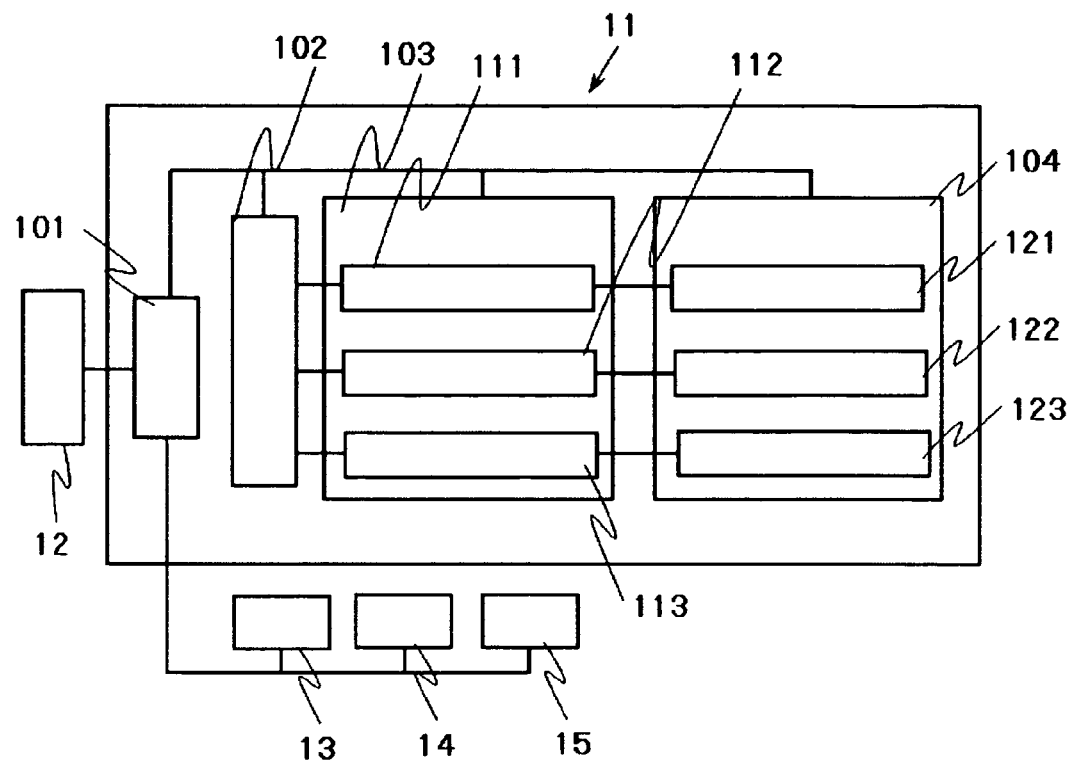
FIG. 2 is a structural diagram of a blood analyzer.

As shown in FIG. 2, the sample analyzer 11 of the blood analyzer 1 includes a control unit 101, sample quantification unit 102, sample preparation unit 103, and sample assay unit 104. The control unit 101 includes a microcomputer provided with RAM, ROM, memory such as a hard disk or the like, and CPU; and a communication controller for sending and receiving data.

The sample quantification unit 102 measures the blood sample mixed and suctioned by the sample mixing/suctioning device 15 from the sample container 26. The sample quantification unit 102 may be formed of three ceramic disks. A flow path through which a blood sample flows may be formed by three ceramic disks, such that the center disk is rotated between the outer two stationary disks, and a suctioned blood sample is quantified by remaining within the center disk flow path the inlet and outlet of which is blocked.

The sample preparation unit 103 includes an erythrocyte sample preparation unit 111 for diluting a blood sample and preparing a sample for erythrocyte/platelet assay, leukocyte sample preparation unit 112 for subjecting a blood sample to hemolysis and preparing a sample for leukocyte assay, and an HGB sample preparation unit 113 for subjecting a blood sample to hemolysis and preparing a sample for HGB (hemoglobin) assay.

The sample assay unit 104 includes an erythrocyte sample assay unit 121 for obtaining a measurement signal by measuring the electrical resistance when a prepared erythrocyte/platelet assay sample passes through an orifice (pore), leukocyte assay unit 122 for obtaining a measurement signal by optically measuring a prepared leukocyte sample using a flow cytometer, and an HGB sample assay unit 123 for obtaining a measurement signal by measuring the light absorption of a prepared HGB sample.

The control unit 101 receives the analysis conditions from the display/operation unit 12 and the output signals from the barcode reader 14, and controls the rack supply unit 13, sample mixing/suctioning device 15, sample quantification unit 102, sample preparation unit 103, and sample assay unit 104.

The control unit 101 receives the measurement signal from the sample preparation unit 104, and calculates the number of erythrocytes contained in the sample, the number and particle size of the leukocytes and platelets, concentration of the hemoglobin (HGB), hematocrit value, mean volume of the erythrocytes (MCV) and the like.

As shown in FIG. 1, the whole blood immunoassay apparatus 2 includes a rack supply unit 23 for supplying one by one a plurality of racks 27 holding sample containers 26, barcode reader 24 for reading the barcode of the sample container 26, sample mixing/suctioning device 25 for mixing and suctioning blood samples of the sample container 26, immunosample analyzer 21 for analyzing suctioned blood samples, and display/operation unit 22 for inputting analysis conditions and outputting assay results. The display/operation unit 22 is a touch panel-type display capable of display and operation (input).

Figure 3:
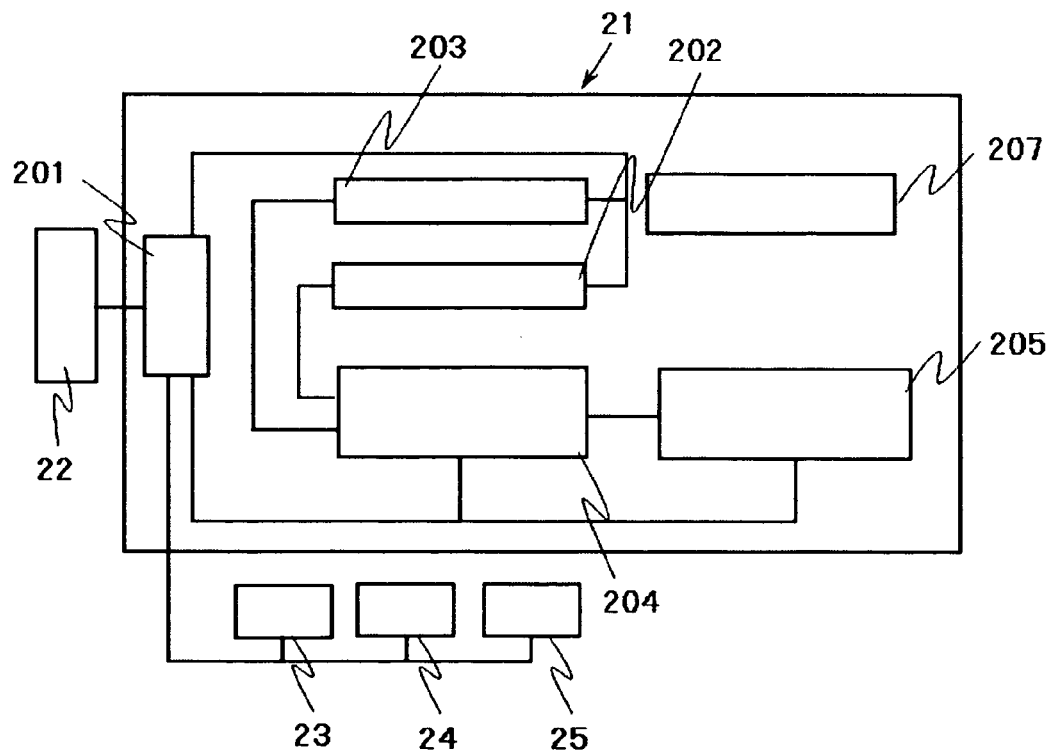
FIG. 3 is a structural diagram of a whole blood immunoassay apparatus.

As shown in FIG. 3, the immunosample analyzer 21 of the whole blood immunoassay apparatus 2 includes a control unit 201, immunosample quantification unit 202, immunoreagent quantification unit 203, immunosample preparation unit 204, immunosample assay unit 205, and immunoreagent feeder unit 207. The control unit 201 includes a microcomputer provided with RAM, ROM, memory such as a hard disk or the like, and CPU; and a communication controller for sending and receiving data.

The immunosample quantification unit 202 measures the blood sample mixed and suctioned by the sample mixing/suctioning device 25 from the sample container 26. The immunosample quantification unit 202 measures the blood sample via a dispenser unit such as a dispenser pipette or the like. The immunoreagent quantification unit 203 measures the immunoreagent via a dispenser unit such as a pipette or the like from the reagent containers 17 and 18 (refer to FIG. 16) held by the reagent feeder 207.

Figures 15, 16:
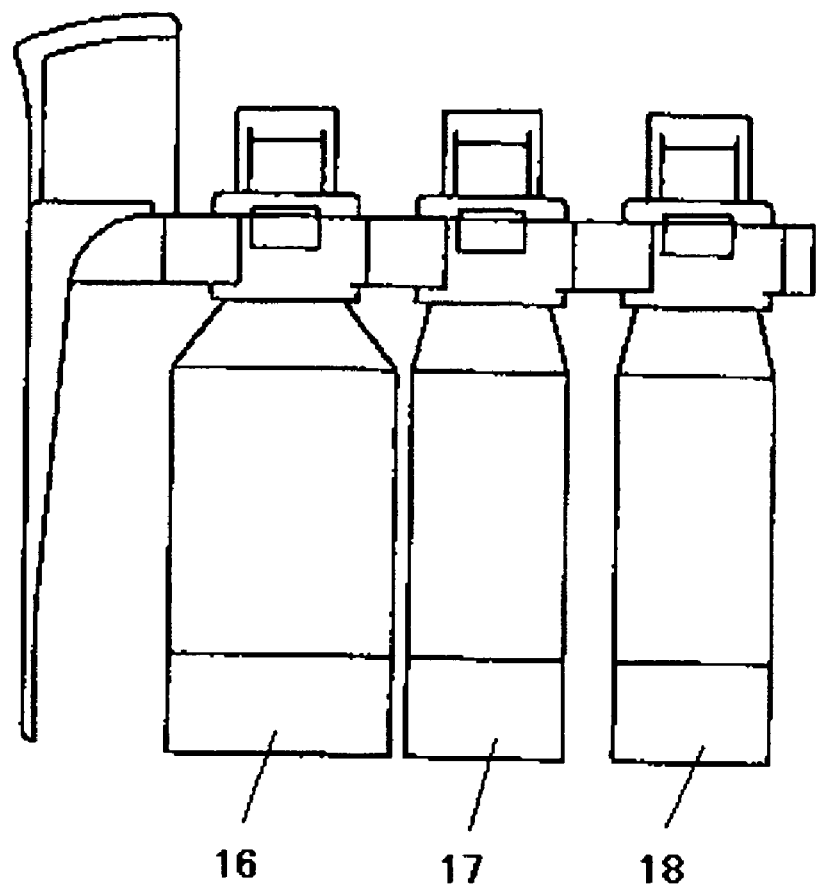
FIG. 15 is a table showing the discrimination results.
FIG. 16 is an immunosample container accommodating an immunoreagent.

The immunosample preparation unit 204 mixes a measured quantity of blood sample (whole blood sample) and immunoreagent to prepare the immunoassay sample. As shown in FIG. 16, the immunoreagent includes the reagent container 16 accommodating a dilution fluid for diluting blood samples, the reagent container 17 for accommodating buffer solution for maintaining the prepared immunoassay sample at a constant pH, and immunoreagent container 18 for accommodating latex reagent sensitized to antigen or antibody.

The immunosample assay unit 205 analyzes the prepared immunoassay sample via a counting immunoassay. The counting immunoassay is an analysis method wherein a latex reagent sensitized for an antibody or antigen is reacted with an antigen or antibody in the sample, the agglutinated particles are discriminated by flow cytometry, and counted.

The control unit 201 receives the output signals of the barcode reader 23 and the analysis conditions of the display/operation unit 22, and controls the rack supply unit 23, sample mixing/suctioning device 25, immunosample quantification unit 202, immunoreagent quantification unit 203, immunosample preparation unit 204, and immunosample assay unit 205.

Furthermore, the control unit 201 receives the assay signals from the sample assay unit 205, and calculates the values of cancer markers and infection markers and the like contained in the sample. Cancer markers and infection markers are calculated as antigen concentration or antibody concentration. Then, correction is performed based on the hematocrit received from the blood analyzer 1 to convert to serum or plasma antigen concentration or antibody concentration.

The control unit 101 of the blood analyzer 1 and the control unit 201 of the whole blood immunoassay apparatus 2 are connected via a communication cable 24, such that assay results obtained by the blood analyzer 1 are transmitted by a communication controller of the control unit 101 from the control unit 101 to the control unit 201 of the whole blood immunoassay apparatus 2 through the communication cable 24. The assay result of the blood analyzer 1 transmitted to the whole blood immunoassay apparatus 2 includes erythrocyte count, hematocrit, mean erythrocyte volume, and platelet count.

Figure 4:
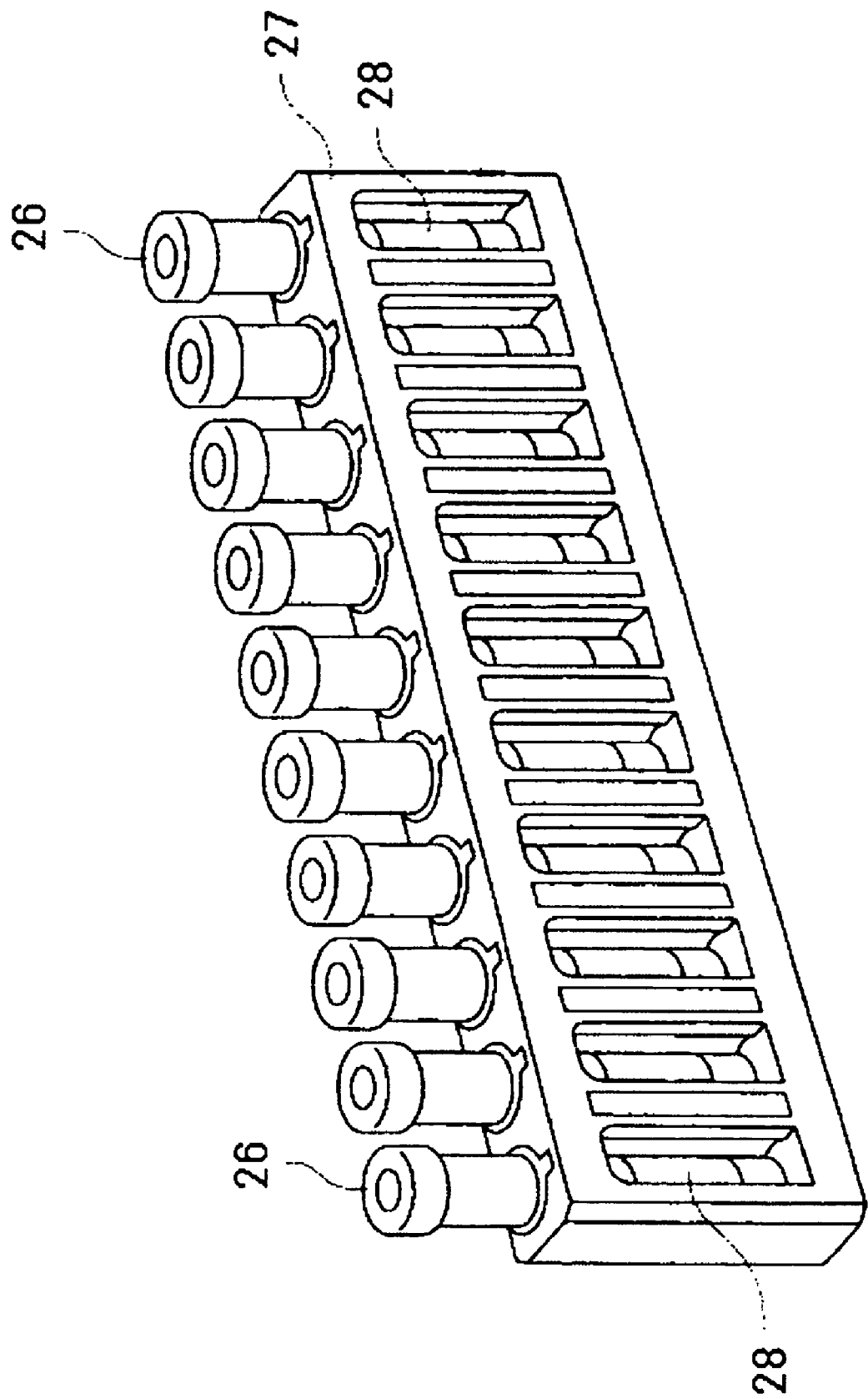
FIG. 4 is a perspective view of a rack.

As shown in FIG. 4, each rack 27 is shaped to hold test tubes upright so as to accommodate 10 test tubes 26. The test tube 26 is a container shaped like a test tube with a closed bottom and an open top end which is covered by a cap, and is capable of internally accommodating blood as a sample, and a barcode label 28 is adhered to the outer surface of the container. The barcode label 28 includes an ID number and the like as information identifying the blood sample (specimen).

The operation of the clinical laboratory test system is described below.

A rack 27 which holds sample containers 26 is loaded in the rack supply unit 13 of the blood analyzer 1. When an assay instruction is input from the display/operation unit 12, the rack 27 on the rack supply unit 13 is moved to the interior. The rack 27 which has been moved to the interior is transversely fed to the left, and the barcode label 28 adhered to the sample container 26 is read by the barcode reader 14. Subsequently, after sample mixing by the sample mixing/suctioning unit 15, the blood sample is suctioned from the sample container 26 by a suction needle. The suctioned blood sample is measured by the sample quantification unit 102, and after the blood sample is subjected to dilution or hemolysis by the sample preparation unit 103, the sample is assayed by the sample assay unit 104. The assay signal obtained by the assay is transmitted to the control unit 101, and after analysis is stored in the memory of the control unit 101 as ID number and assay data. Furthermore, by setting automatic transmission of the assay data, the control unit 101 sends the assay data to the control unit 201 of the whole blood immunoassay apparatus 2 through the communication cable 24 via the communication controller of the control unit 101 at the same time as the assay result is output to the display/operation unit 12.

The assay data transmitted to the whole blood immunoassay apparatus 2 includes erythrocyte count, hematocrit, mean erythrocyte volume (MCV) platelet count (PLT) and the like.

The control unit 201 of the whole blood immunoassay apparatus 2 which received the assay data stores the ID number and assay data in the memory of the control unit 201. The assay data stored in the memory stores the erythrocyte count, hematocrit, platelet count, and MCV corresponding to ID number, as shown in FIG. 17. Furthermore, an anomaly determination table for determining whether or not the specimen can be subjected to whole blood immunoassay by the whole blood immunoassay apparatus 2 is stored beforehand in the memory of the control unit 201, as shown in FIG. 5. The anomaly determination table shown in FIG. 5 shows a threshold 302 corresponding to assay item 301, anomaly determination equation 303 representing when the threshold is exceeded or not met, and anomaly value 304 for when the anomaly determination equation applies.

Figure 6:
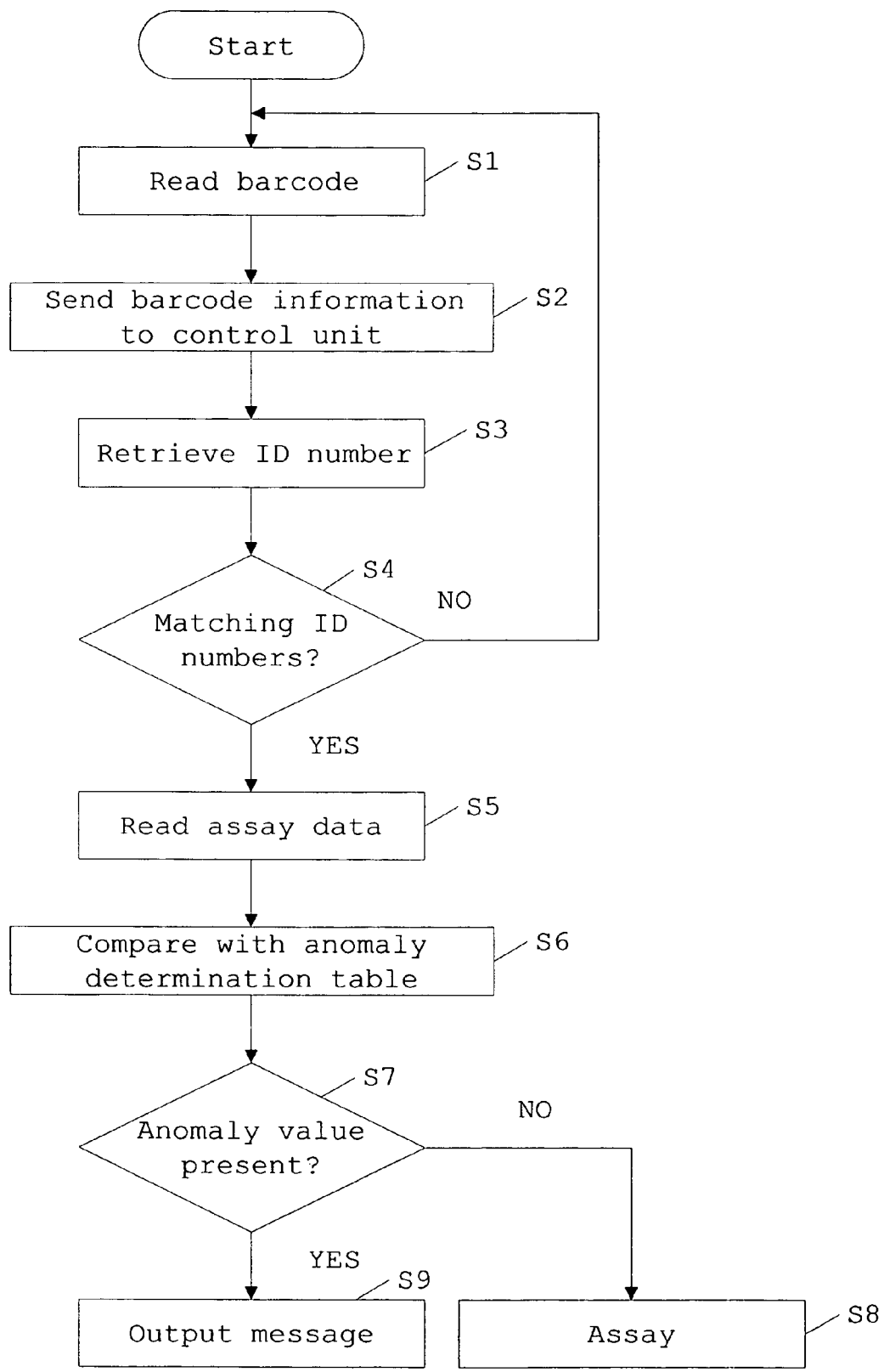
FIG. 6 is an illustration representing the message output flow.

The assay operation of the whole blood immunoassay apparatus 2 executed by the control unit 201 is described below using the flow chart of FIG. 6. The sample container 26 which has been assayed by the blood analyzer 1 is set in the rack supply unit 23 of the whole blood immunoassay apparatus 2. The barcode label 28 of the placed sample container 26 is read by the barcode reader 24, and the ID number is transmitted to the control unit 201 (steps S1 and S2). The control unit 201 retrieves the assay data of the same ID number receives from the blood analyzer 1 from the memory of the control unit 201 (refer to FIG. 17) (step S3). Then it is determined whether or not the ID number of the retrieved result matches the ID number (step S4). When the ID numbers do not match, the routine returns to the step of reading the barcode label 28 of the next sample container 26 (step S1). When the ID numbers match, the assay data of that ID number are read from the memory of the control unit 201 (step S5). A determination is made as to whether or not the read assay data contains anomaly value by referring to the anomaly determination table (refer to FIG. 5) within the memory of the control unit 201.

When an anomaly value is not determined, the blood sample in the sample container 26 corresponding to the assay data is determined to be suitable for whole blood assay, and the blood sample in the sample container 26 is assayed (step S8). A fixed quantity of the blood sample is suctioned from the sample container 26 by the immunosample quantification unit 202, and a fixed quantity of reagent is suctioned by the immunoreagent quantification unit 203. The suctioned blood sample and reagent are transported to the immunosample preparation unit 204, to prepare the whole blood immunoassay sample. The prepared whole blood immunoassay sample is transported to the immunosample assay unit 205 and assayed. In the control unit 201, correction is performed based on the hematocrit transmitted from the blood analyzer 1 to convert the assay data to antigen concentration or antibody concentration of the serum or plasma. The assay result is output to the display/operation unit 22.

Figure 7:
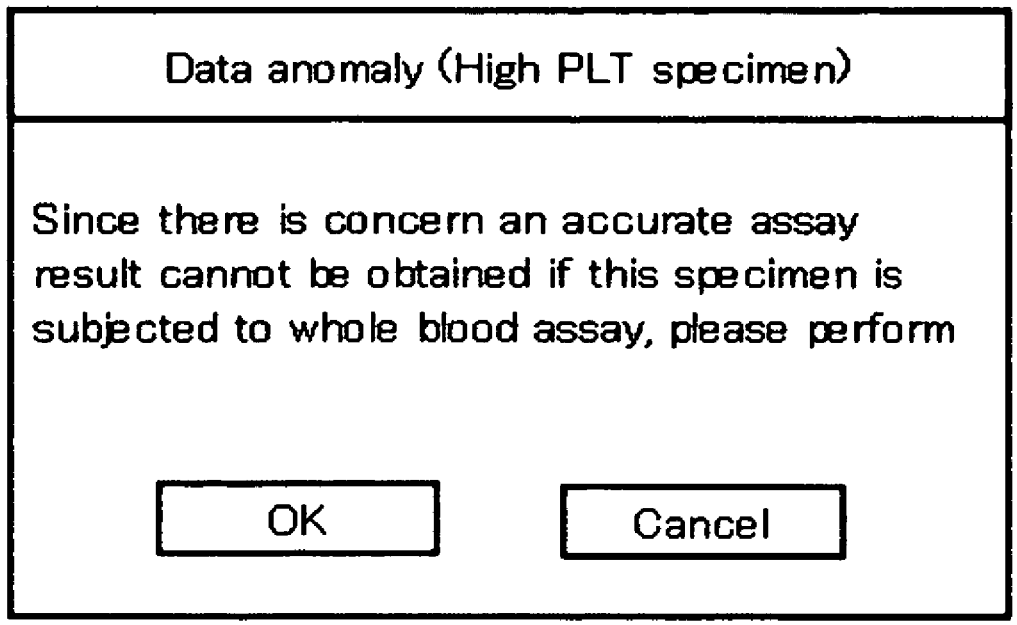
FIG. 7 is an illustration of a message.

When an anomaly value is determined, the blood sample in the sample container 26 corresponding to the assay data is determined to be unsuited for whole blood immunoassay, and the display screen (message) shown in FIG. 7 is output to the display-operation unit 22 (step S9). This display screen shows an example of high level PLT specimen (high level platelet specimen). The assay technician promptly performs the following measures when the specimen is determined to be unsuitable based on this display screen. Specifically the specimen is centrifuged and the plasma is subjected to immunoassay, and a blood collection order is again output and the serum of the new specimen is subjected to immunoassay.

Figure 8:
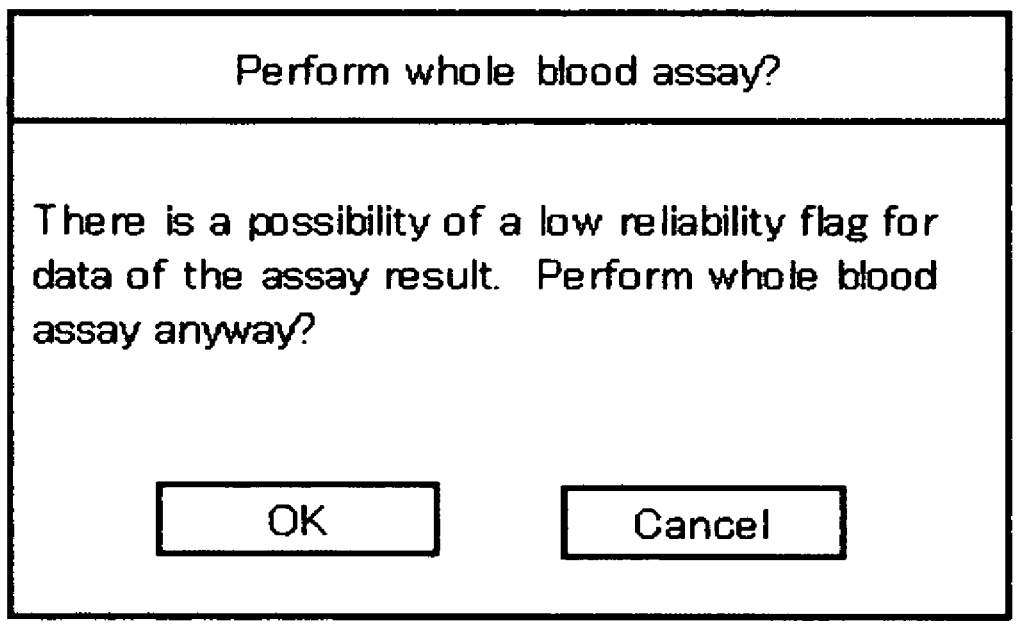
FIG. 8 is an illustration of a message.

Furthermore, there may be times during the whole blood immunoassay when an assay is needed on an emergency basis even though assay data reliability is low. For example, when the hematocrit value is high, MCV (mean erythrocyte volume) value is high, or the MCV value is low, the display screen (message) shown in FIG. 8 is output to the display/operation unit 22, and the assay technician determines whether or not to perform an assay. In the state in which the display screen shown in FIG. 8 is displayed on the display/operation unit 22, the operation of the whole blood immunoassay apparatus 2 is stopped, and unless the technician performs an operation, the apparatus cannot proceed to the next operation. When the user pushes the OK button on the display screen shown in FIG. 8, the whole blood immunoassay of the specimen begins. When the user presses the cancel button, the whole blood immunoassay of the specimen is not performed, and a determination is made as to whether or not whole blood immunoassay is possible for the next specimen.

In the immunoassay of the infection items, serum is typically used as the assay sample, however, a problem arises inasmuch as approximately 30 min is required to obtain the whole blood or serum. Furthermore, in the whole blood immunoassay apparatus, a problem arises inasmuch as suitable assay data may not be obtained from the specimen.

In the first embodiment, a determination is made as to whether or not a specimen is suitable for assay in the whole blood immunoassay apparatus 2 before the specimen is assayed based on assay data of the specimen (whole blood) obtained by the blood analyzer 1. In this way the operator can rapidly determine to perform an immunoassay using the whole blood immunoassay apparatus, or perform an immunoassay using serum.

In the first embodiment, the display/operation units 12 and 22 are touch panel type displays capable of both display and operation (input), however, in another embodiment the structures may be separated into input units and output units. A keyboard, mouse, ten-key pad, and touch-key pad and the like may be used as input devices, and display devices such as CRT, LCD and the like, printing devices such as printers and the like, and sound output devices may be used as output devices.

Furthermore, in the first embodiment, the leukocyte assay unit 122 is constructed so as to obtain an assay signal by optical measurement using a flow cytometer, however, the leukocyte assay unit 122 may be constructed so as to obtain an assay signal by measuring electrical resistance when the leukocyte sample passes through an orifice (pore).

Although the immunosample assay unit 205 is constructed so as to perform analysis by a counting immunoassay of a prepared immunoassay sample in the first embodiment, the immunosample assay unit 205 may be constructed so as to perform analysis by the change in light absorption or change in scattered light by exposing to light an immunoassay sample containing agglutinated particles produced by antigen/antibody reaction.

Although the control unit 201 performs correction based on the hematocrit transmitted from the blood analyzer 1 to convert the assay data to antigen concentration or antibody concentration in serum or plasma in the first embodiment, the control unit 201 also may perform correction by the erythrocyte count measured by the immunosample assay unit 205 to convert the assay data to the antigen concentration or antibody concentration in the serum or plasma.

Second Embodiment

Figure 9:
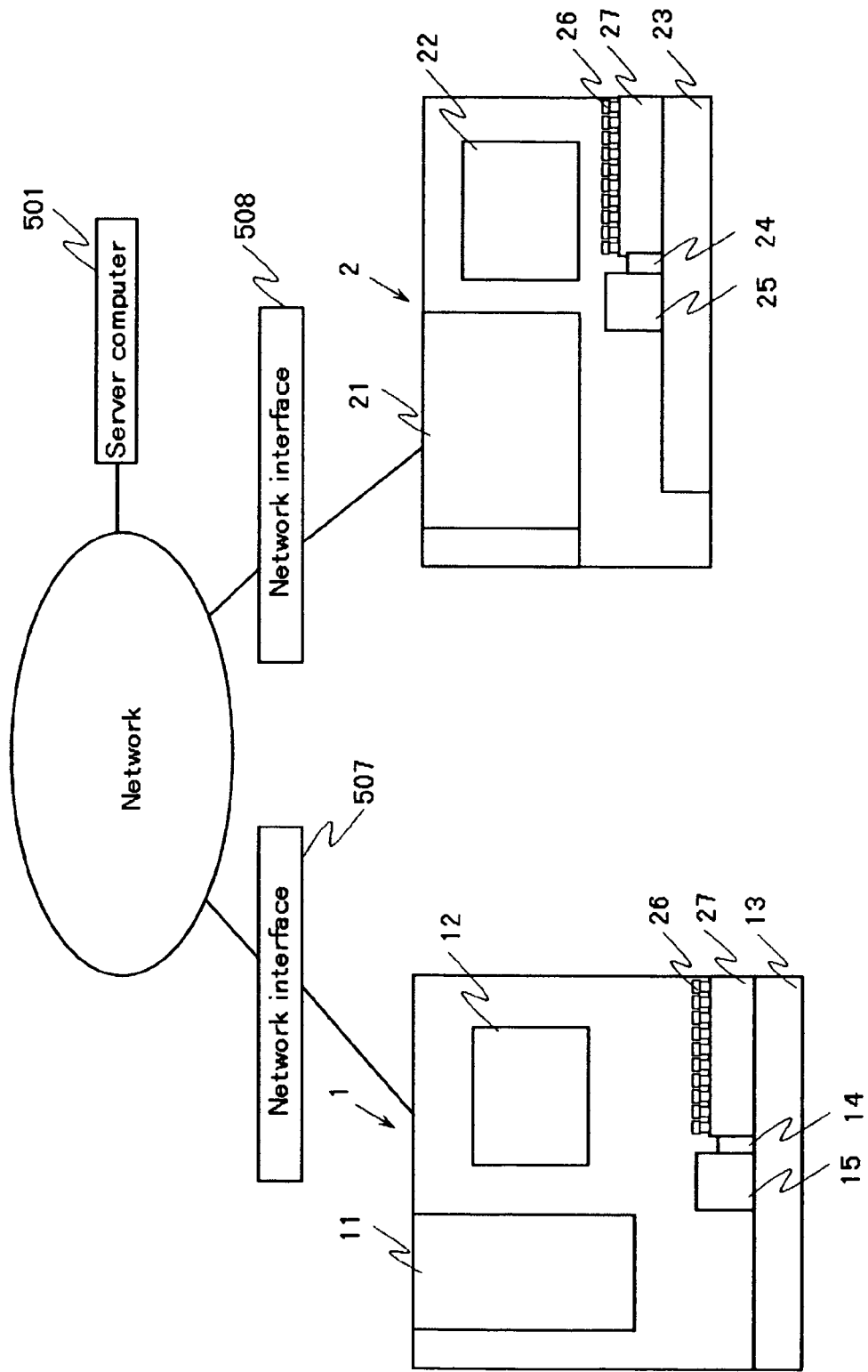
FIG. 9 is an exterior view of a second embodiment of the system.

FIG. 9 is an exterior view showing a second embodiment of the system including a whole blood immunoassay apparatus. In FIG. 9, descriptions of the parts corresponding to parts in FIG. 1 are omitted and such parts are given similar reference numbers. This system includes a blood analyzer 1 connected to a network interface 507, and a whole blood immunoassay apparatus 2 connected to a network interface 508, which are connected to a server computer 501 over a network such as the internet.

Figure 10:
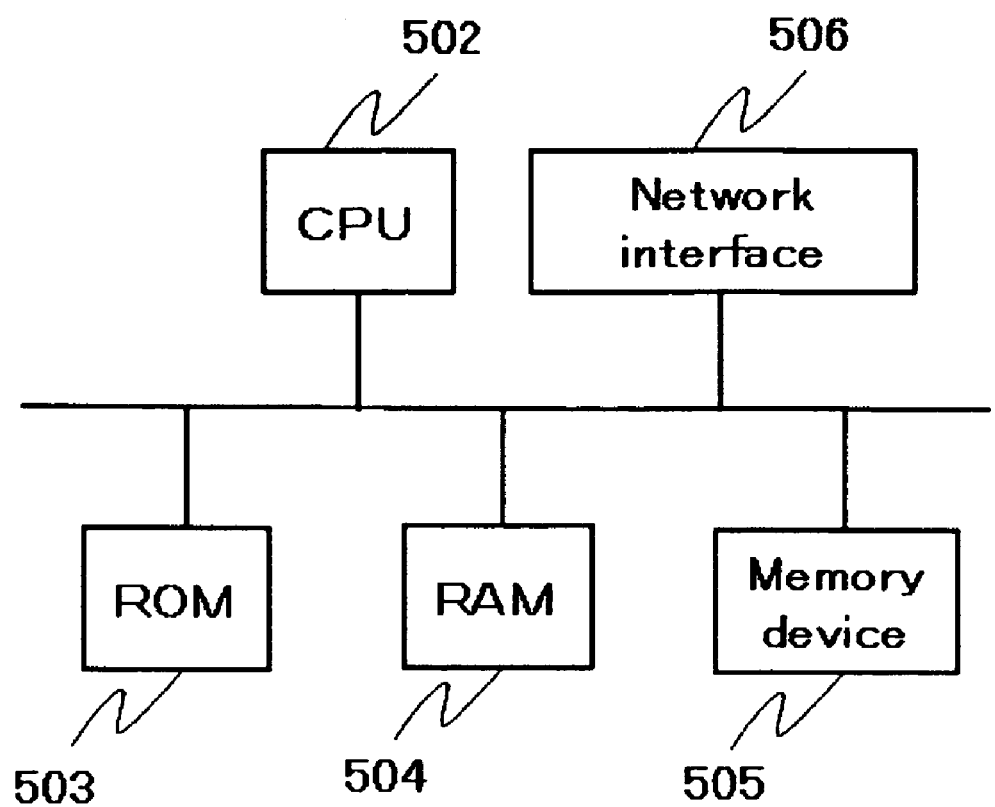
FIG. 10 is an illustration showing the message output flow.

As shown in FIG. 10, the server 501 includes a CPU 502 for reading programs and performing processes, ROM 503 in which is stored beforehand the control sequence of the CPU 502, RAM 504 which is used by the CPU 502 when performing processing, memory device 505 which is a recording medium for supplying program code, and network interface 506 used when connecting to the network. The network interface is a general purpose TCI/IP interface (transmission control protocol/internet protocol).

The structures of the blood analyzer 1 and whole blood immunoassay apparatus 2 are identical to those shown in FIGS. 2 and 3 and further descriptions are omitted.

The operation of the clinical laboratory test system is described below.

When a rack 27 is placed in the rack supply unit 13 of the blood analyzer 1, the barcode of the sample container 26 is read by the barcode reader 14, the blood sample in the sample container 26 is analyzed, and the ID number and assay data are saved to the memory of the control unit 101. Since automatic transmission of the assay data is set, when the control unit 101 transmits the ID number and assay data from the memory to the server computer 501 over the network via the network interface 507, the CPU 502 stores the ID number and assay data in the memory device 505. The assay data stored in the memory device 505 are erythrocyte count, hematocrit, platelet count, and MCV corresponding to the ID number identical to that stored in the memory of the control unit 201, as shown in FIG. 17.

Figure 11:
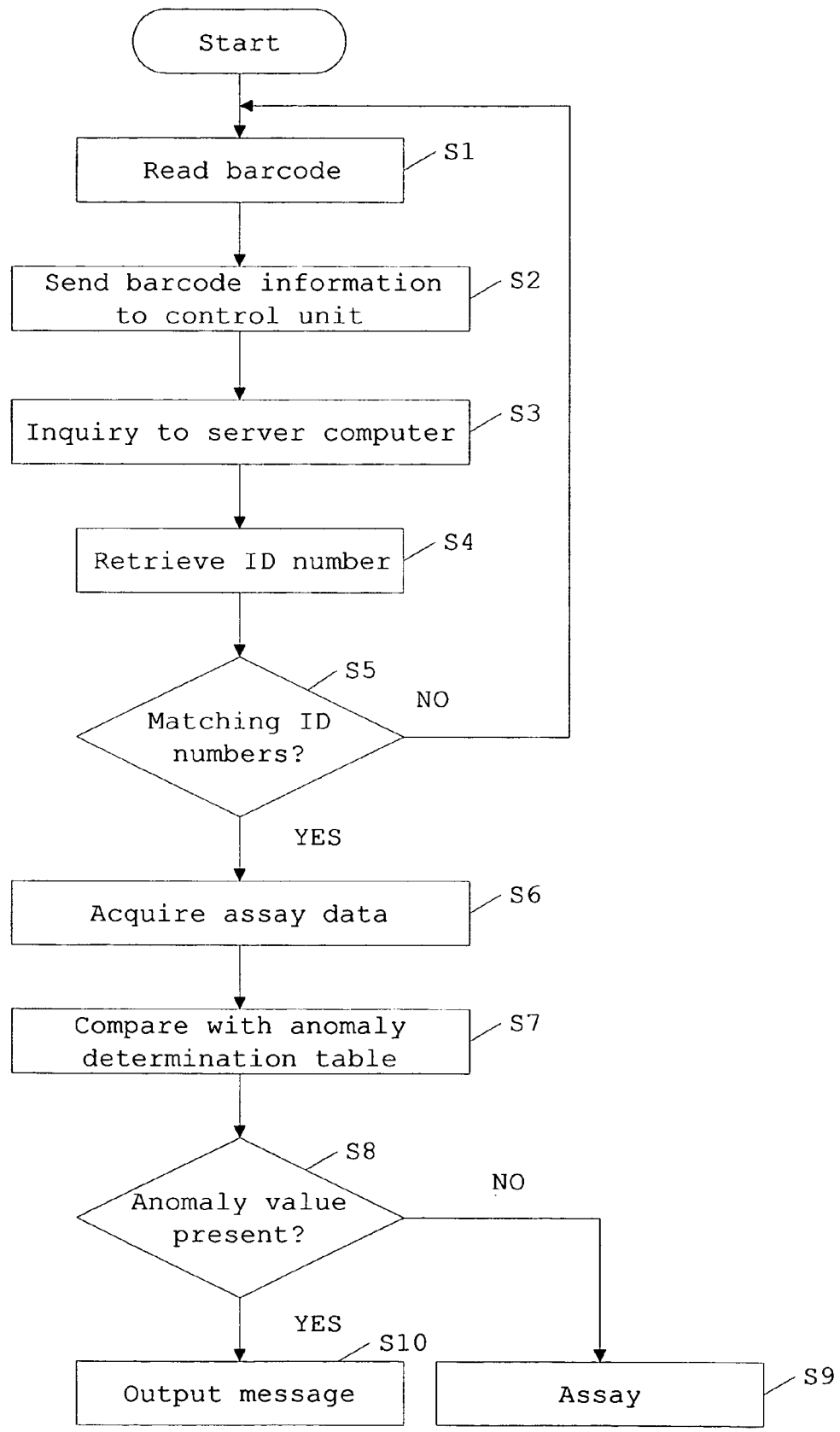
FIG. 11 is an external view of a third embodiment of the system.

The assay operation of the whole blood immunoassay apparatus 2 executed by the control unit 201 is described below using the flow chart of FIG. 11. When the rack 27 is placed in the rack supply unit 23, the barcode label 28 of the sample container 26 is read by the barcode reader 24, and information including the ID number is transmitted to the control unit 201 (steps S1 and S2). The control unit 201 of the whole blood immunoassay apparatus 2 inquires to the server computer 501 for the ID number (step S3). The CPU 502 of the server computer 501 retrieves the assay data of the same ID number received from the blood analyzer 21 from the memory device 505 (step S4). A determination is made as to whether or not there are assay data which match the ID number (step S5). When there are no assay data matching the ID number, the CPU 502 of the server computer transmits the determination result to the control unit 201 of the whole blood immunoassay apparatus 2 over the network interface 506, and control unit 201 issues instructions to read the barcode label 28 of the next sample container 26 (step 1). When there are assay data with matching ID number, the CPU 502 of the server computer transmits the ID number and assay data from the memory device 505 to the control unit 201 of the whole blood immunoassay apparatus 2, and the control unit 201 acquires the assay data having that ID number, and stores the assay data in the control unit 201 (step S6). The control unit 201 compares the anomaly determination table (refer to FIG. 5) and the assay data stored in the memory of the control unit 201, and determines whether or not there is an anomaly value (step S7, S8).

When it is determined that there is no anomaly value, the blood sample in the sample container 26 corresponding to the assay data is determined to be suitable for whole blood assay, and the blood sample in the sample container 26 is assayed (step S9). A fixed quantity of the blood sample is suctioned from the sample container 26 by the immunosample quantification unit 202, and a fixed quantity of reagent is suctioned from the immunoreagent quantification unit 203. The suctioned blood sample and reagent are transported to the immunosample preparation unit 204, and the whole blood immunosample is prepared. The prepared whole blood immunoassay sample is transported to the sample assay unit 205 and assayed. In the control unit 201, correction is performed based on the hematocrit transmitted from the blood analyzer 1 to convert the assay data to antigen concentration or antibody concentration in the serum or plasma. The assay result is output to the display/operation unit 22.

When it is determined there is an anomaly value, it is determined that the blood sample in the sample container 26 corresponding to the assay data is unsuited for whole blood immunoassay, and the display screen shown (message) in FIG. 7 is output to the display/operation unit 22 (step S10). This display screen shows an example of a high level PLT specimen (high level platelet specimen).

In the second embodiment, the blood analyzer 1 and whole blood immunoassay apparatus 2 are connected to the server computer 501 over a network, however, the blood analyzer 1 and whole blood immunoassay apparatus 2 also may be connected directly over a network. In this case, the network represents a communication line such as the internet, intranet, inthernet and the like.

Although the blood analyzer 1 and whole blood immunoassay apparatus 2 are respectively connected to a network through network interfaces 507 and 508 in the second embodiment, the control unit 101 of the blood analyzer 1 and the control unit 201 of the whole blood immunoassay apparatus 2 also may incorporate network interfaces.

In this way information can be transmitted between devices in different locations by connecting the blood analyzer 1 and whole blood immunoassay apparatus 2 through a network, and it is possible for the whole blood immunoassay apparatus 2 to determine whether or not a target specimen is suitable for whole blood immunoassay based on the assay data of the blood analyzer 1.

Third Embodiment

Figure 12:
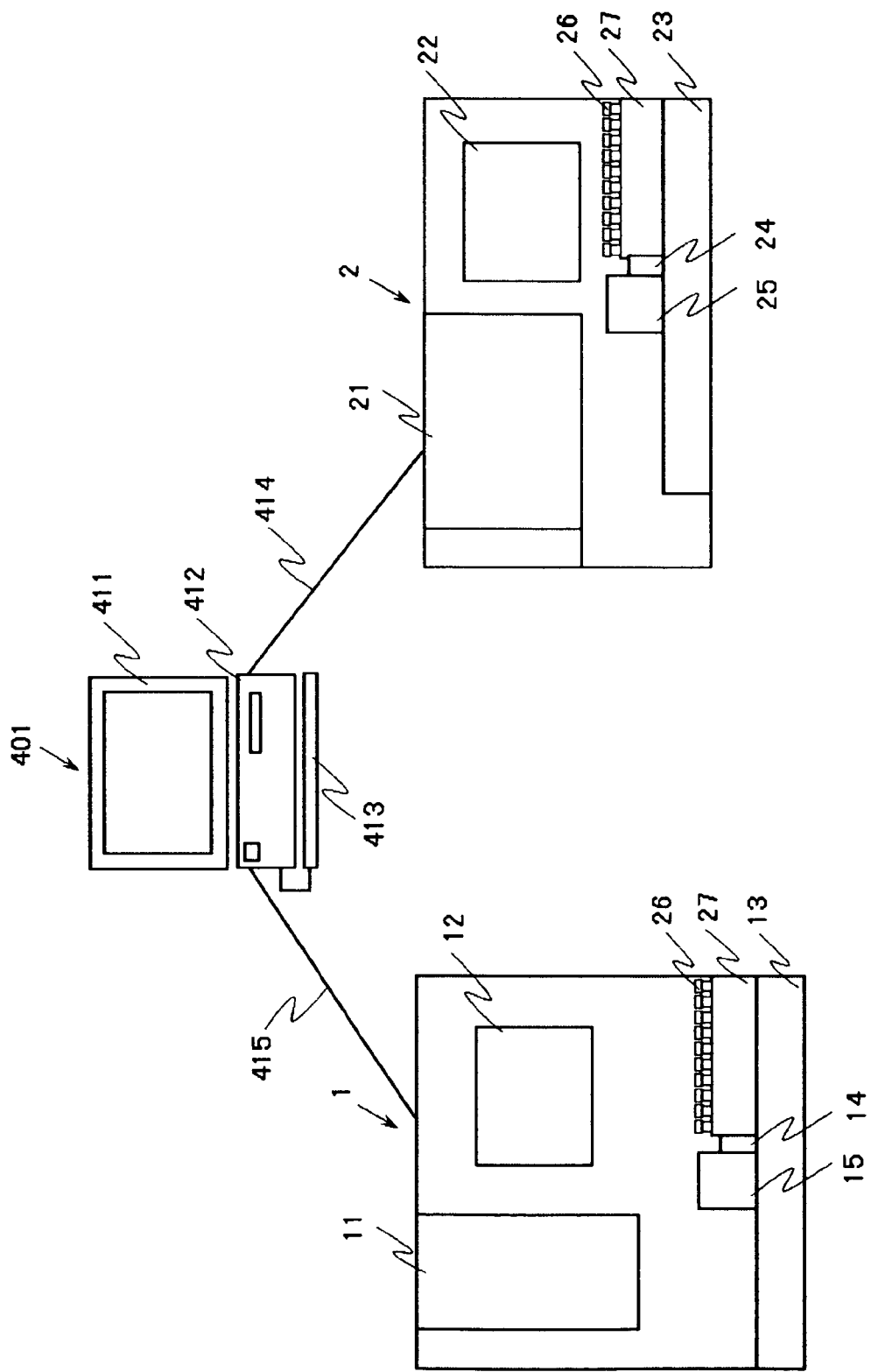
FIG. 12 is a structural diagram of a server computer.

FIG. 12 is an exterior view of the third embodiment of the system including a whole blood immunoassay apparatus. In FIG. 12, descriptions of the parts corresponding to parts in FIG. 1 are omitted and such parts are given similar reference numbers. This system includes a blood analyzer 1 connected to a host computer 401, and a whole blood immunoassay apparatus 2 connected to the host computer 401 by communication cables 415 and 416, respectively.

As shown in FIG. 12, the host computer 401 includes control unit 412 provided with a memory for storing specimen assay data transmitted from the blood analyzer 1, CRT 411 for displaying assay data and the determination result as to whether or not whole blood immunoassay is possible, and keyboard 413 for inputting assay conditions and assay data. The control unit 401 includes a microcomputer provided with RAM, ROM, memory such as a hard disk or the like, and CPU; and a communication controller for sending and receiving data.

The structures of the blood analyzer 1 and whole blood immunoassay apparatus 2 are identical to those shown in FIGS. 2 and 3 and further descriptions are omitted.

The operation of this specimen laboratory test system is described below.

When the rack 27 is placed in the rack supply unit 13 of the blood analyzer 1, the barcode 28 of the sample container 26 is read by the barcode reader 14, the blood sample in the sample container 26 is analyzed, and the ID number and assay data are saved in the memory of the control unit 101. Since automatic transmission of the assay data is set, when the control unit 101 transmits the ID number and assay data from the memory to the host computer 401 over the communication cable 415 via the communication controller of the control unit 101, the control unit 412 stores the ID number and assay data in the memory of the control unit 412. The assay data stored in the control unit 412 are erythrocyte count, hematocrit, platelet count, and MCV corresponding to the ID number identical to that stored in the memory of the control unit 201, as shown in FIG. 17.

Figure 13:
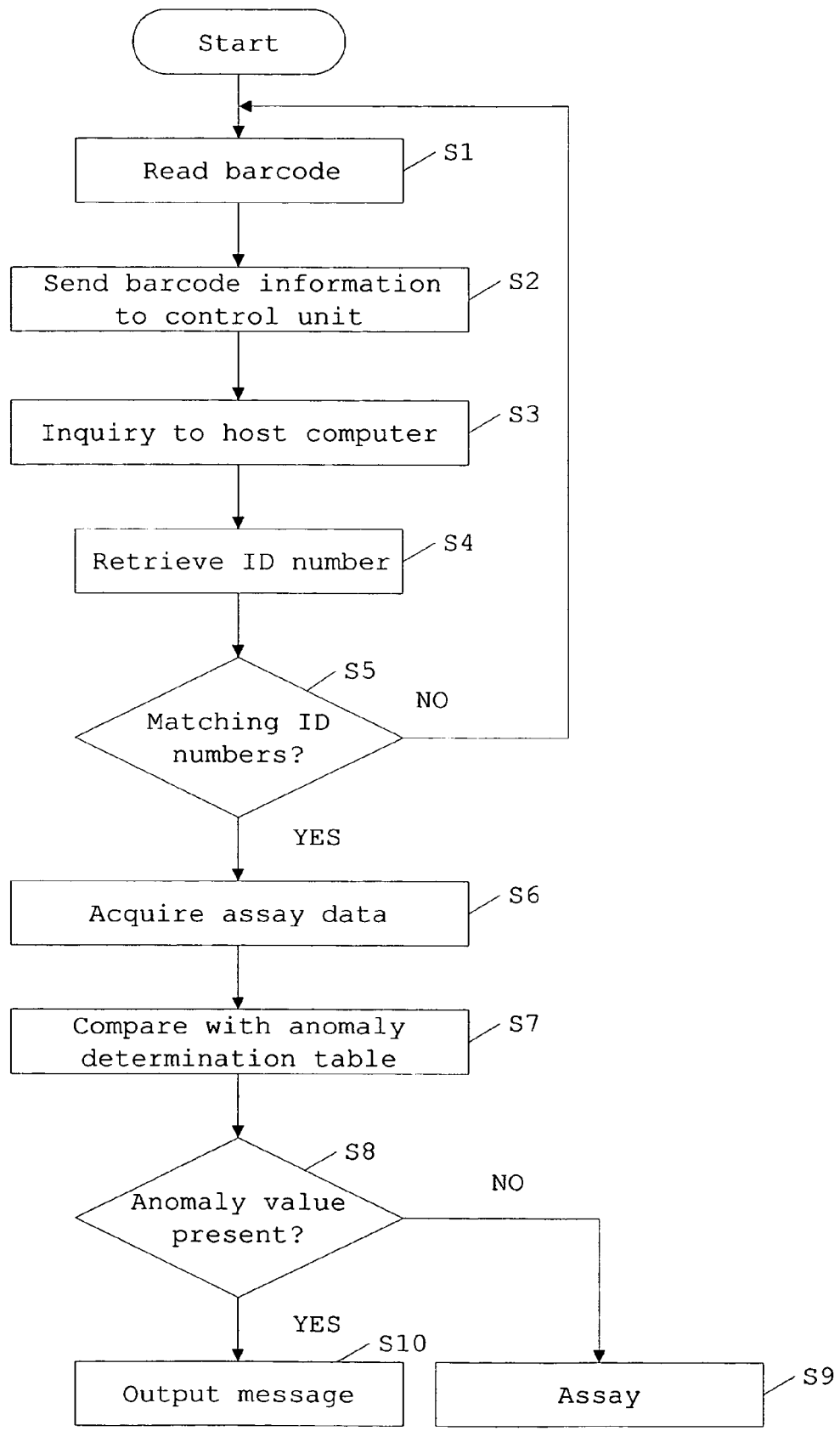
FIG. 13 is an illustration showing the message output flow.

The assay operation of the whole blood immunoassay apparatus 2 executed by the control unit 201 is described below using the flow chart of FIG. 13. When the rack 27 is placed in the rack supply unit 23, the barcode label 28 of the sample container 26 is read by the barcode reader 24, and the ID number is transmitted to the control unit 201 (steps S1 and S2). The control unit 201 of the whole blood immunoassay apparatus 2 inquires to the host computer 401 for the ID number (step S3). The control unit 412 of the host computer retrieves the assay data of the same ID number received from the blood analyzer 21 from the memory of the control unit 412 (step S4). A determination is made as to whether or not there are assay data which match the ID number (step S5). When there are no assay data matching the ID number, the control unit 412 of the host computer transmits the determination result to the control unit 201 of the whole blood immunoassay apparatus 2 via the communication controller of the control unit 412, and control unit 201 issues instructions to read the barcode label 28 of the next sample container 26 (step 1). When there are assay data with matching ID number, the communication controller of the control unit 412 of the host computer transmits the result to the control unit 201 of the whole blood immunoassay apparatus 2, and the control unit 201 acquires the assay data having that ID number, and stores the assay data in the memory of the control unit 201 (step S6). The control unit 201 compares the anomaly determination table (refer to FIG. 5) and the assay data stored in the memory of the control unit 201, and determines whether or not there is an anomaly value (step S7, S8).

When it is determined that there is no anomaly value, the specimen in the sample container 26 corresponding to the assay data is determined to be suitable for whole blood assay, and the blood sample in the sample container 26 is assayed (step S9). A fixed quantity of the blood sample is suctioned from the sample container 26 by the immunosample quantification unit 202, and a fixed quantity of reagent is suctioned from the immunoreagent quantification unit 203. The suctioned blood sample and reagent are transported to the immunosample preparation unit 204, and the whole blood immunosample is prepared. The prepared whole blood immunoassay sample is transported to the sample assay unit 205 and assayed. In the control unit 201, correction is performed based on the hematocrit transmitted from the blood analyzer 1 to convert the assay data to antigen concentration or antibody concentration in the serum or plasma. The assay result is output to the display/operation unit 22.

When it is determined there is an anomaly value, it is determined that the blood sample in the sample container 26 corresponding to the assay data is unsuited for whole blood immunoassay, and the display screen (message) shown in FIG. 7 is output to the display/operation unit 22 (step S10). This display screen shows an example of a high level PLT specimen (high level platelet specimen).

Although the blood analyzer 1 and host computer 401, and the whole blood immunoassay apparatus 2 and the host computer 401 are respectively connected via communication cables 415 and 416 in the third embodiment, they also may be connected over a network instead of communication cables. For example, the network may be a communication line such as the internet, intranet, inthernet or the like. Furthermore, assay data of the blood analyzer 1 also may be input to the host computer 401 from the keyboard 413.

Furthermore, in the third embodiment, the host computer 401 is constructed so as to transmit assay data assayed by the blood analyzer 1 to the whole blood immunoassay apparatus 2, however, the host computer 401 may receive assay data assayed by the blood analyzer 1, and determine whether or not the assay data is suited for whole blood immunoassay, and thereafter transmit the determination result to the whole blood immunoassay apparatus 2. Furthermore, the host computer 401 may receive assay data from the blood analyzer 1, determine whether or not the sample is suited for whole blood immunoassay, and thereafter output a display screen (message) as to whether or not the sample is suited for whole blood immunoassay to the CRT 411 of the host computer 401.

In this way assay data from the blood analyzer 1 accumulates in the host computer 401 by having the host computer 401 disposed between the blood analyzer 1 and the whole blood immunoassay apparatus 2, such that assay data or determination results as to whether or not a sample is suited for whole blood immunoassay based on the assay data can be transmitted from the host computer 401 to the whole blood immunoassay apparatus 2. With such a structure, it is possible to manage many clinical laboratory test apparatuses.

Fourth Embodiment

Figure 14:
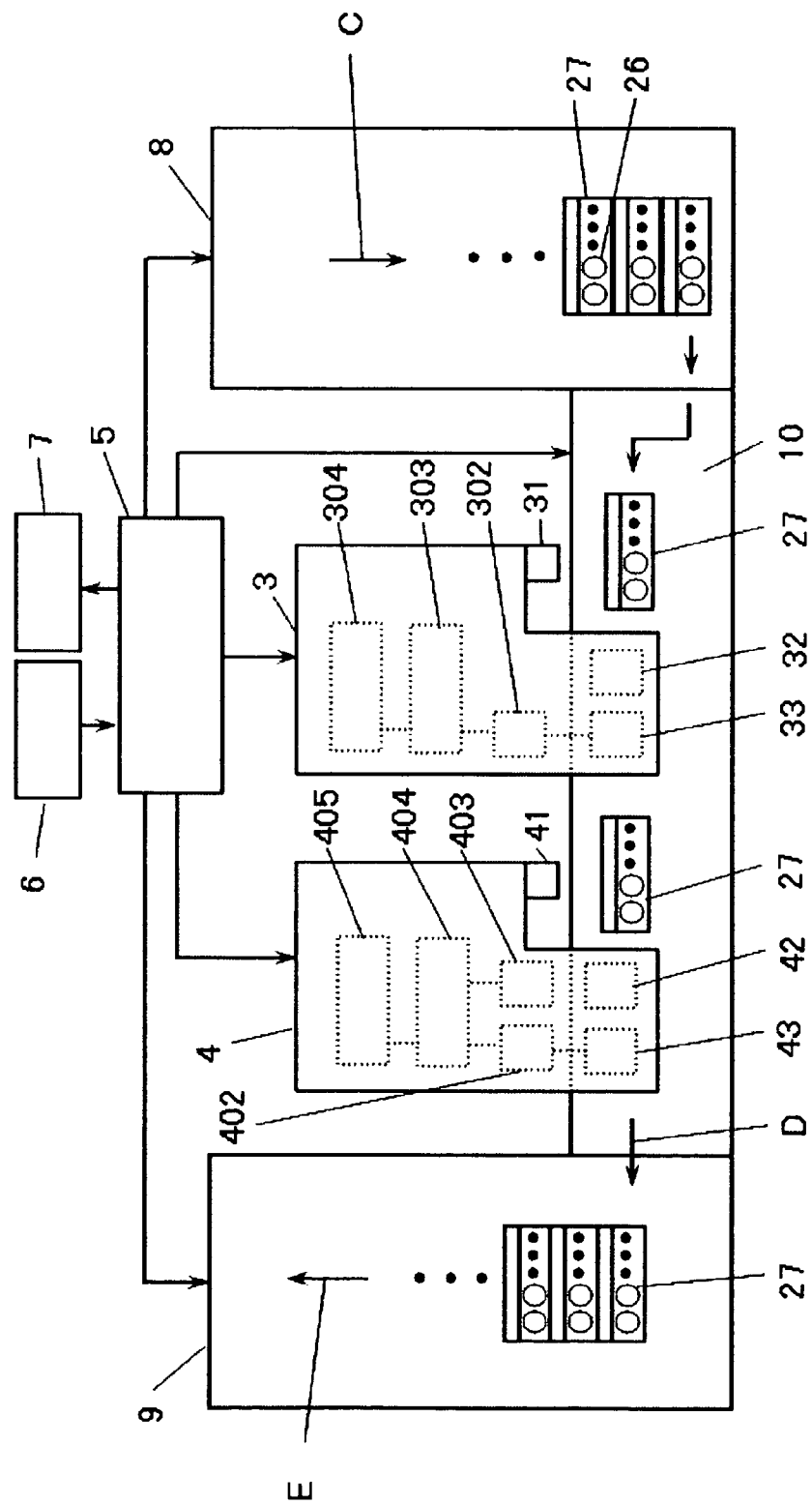
FIG. 14 is a structural diagram of a fourth embodiment of the system

FIG. 14 is a structural diagram showing a fourth embodiment of a system including a whole blood immunoassay apparatus.

A blood analyzer 3 and whole blood immunoassay apparatus 4 are disposed in the center of this clinical laboratory test system; a rack feed unit 8 for transporting one by one a plurality of racks 27 holding sample containers 26 is provided on the right side, and a rack collection unit 9 for collecting the racks 27 is provided on the left side. A rack feed unit 10 for transversely feeding one by one the racks 27 from the rack feed unit 8 to the rack collection unit 9 is provided between the units 8 and 9.

The blood analyzer 3 includes a barcode reader 31 for reading the barcode label 28 of the sample container 26, sample mixing device 32 for mixing the blood sample in the sample container 26, suction device 33 for suctioning a mixed blood sample from the sample container 26, sample quantification unit 302 for measuring the suctioned blood sample, sample preparation unit 303 for preparing a measured blood sample, and assay unit 304 for assaying the measured blood sample.

The sample preparation unit 303 has the same construction as the sample preparation unit 103 of FIG. 2, and includes an erythrocyte sample preparation unit for diluting a blood sample and preparing a sample for erythrocyte/platelet assay, leukocyte sample preparation unit for subjecting a blood sample to hemolysis and preparing a sample for leukocyte assay, and an HGB sample preparation unit for subjecting a blood sample to hemolysis and preparing a sample for HGB (hemoglobin) assay. Since these structures are identical to those in FIG. 2, detailed descriptions are omitted. [0086] The whole blood immunoassay apparatus 4 includes a barcode reader 41 for reading the barcode label 28 of the sample container 26, sample mixing device 42 for mixing the blood sample in the sample container 26, suction device 43 for suctioning the mixed blood sample from the sample container 26, immunosample quantification unit 402 for measuring the suctioned blood sample, immunoreagent quantification unit 403 for measuring the immunoassay reagent, immunosample preparation unit 404 for preparing an analysis sample from the measured blood sample and reagent, and immunosample assay unit 405 for assaying the prepared sample. Since the immunosample quantification unit 402, immunoreagent quantification unit 403, immunosample preparation unit 404, and immunosample assay unit 405 have the same construction as shown in FIG. 3, detailed descriptions are omitted.

The control unit 5 receives the output signals from the barcode readers 31 and 41 and the input unit 6 for inputting analysis conditions, and controls the rack supply unit 8, rack feed unit 10, rack collection unit 9, blood analyzer 3, and whole blood immunoassay apparatus 4. The control unit 5 includes a microcomputer provided with RAM, ROM, memory such as a hard disk or the like, and CPU; and a communication controller for sending and receiving data.

Furthermore, the input unit 6 includes a keyboard and mouse. The output unit 7 is a CRT. The rack feed unit 10 is a unit for transverse feeding formed by a lever for rotational movement provided on the bottom surface of the transport path for transporting the specimen rack, the lever being inserted into a concavity formed in the bottom surface of the specimen rack.

The operation of the clinical laboratory test system is described below.

As shown in FIG. 14, when the a plurality of racks 27 holding sample containers 26 are arrayed in vertical rows on the rack feed unit 8, all the racks 27 are lined up and advance in the direction indicated by the arrow C, and thereafter, the lead rack 27 is transversely fed to the rack feed unit 10.

The rack 27 transported by the rack feed unit 10 is stopped when the lead sample container 26 is at a position opposite the barcode reader 31. When the barcode reader 31 reads the barcode label 28 of the lead sample container 26, the sample container 26 again transversely transported and stopped directly below the sample mixing device 32 of the blood analyzer 3.

Then, when the blood sample in the lead sample container 26 is mixed by the sample mixing device 32, the rack 27 is moved only a predetermined distance (array pitch of the sample containers 26), and the blood sample from the sample container 26 which is completely mixed is suctioned by the sample suction device 33.

The suctioned blood sample is measured by the sample quantification unit 302, an assay sample is prepared by the sample preparation unit 303, and the prepared assay sample is assayed by the sample assay unit 304. During the suction operation of the sample suction device 33, the sample mixing device 32 mixes the sample of the next sample container 26.

The rack 27 intermittently transports the sample containers 26 one by one, and the barcode labels 28 of the sample containers 26 are sequentially read by the barcode reader 41 of the whole blood immunoassay apparatus 4. After temporarily storing the ID number and assay data of the blood analyzer 3 in the memory of the control unit 5, the control unit 5 compares the assay data and anomaly determination table (refer to FIG. 5), determines whether or not the sample is suited for whole blood immunoassay, and stores the ID number and determination result in the memory of the control unit 5.

When the barcode label 28 of the sample container 26 is read by the barcode reader 41 of the whole blood immunoassay apparatus 4, the control unit 5 retrieves the determination result stored in the memory of the control unit 5 based on the ID number, and determines whether or not the blood sample in the sample container 26 is suited for whole blood immunoassay.

When the blood sample in the sample container 26 is determined to be suitable for whole blood immunoassay, the control unit 5 controls the rack feed unit 10, and stops the relevant sample container 26 directly below the sample mixing device 42 of the whole blood immunoassay apparatus 4. Then, after the sample container 26 has been mixed by the sample mixing device 42, the rack 27 is moved only a predetermined distance, and the blood sample is suctioned from the thoroughly mixed sample container 26 by the sample suction device 43. The suctioned blood sample is measured by the immunosample quantification unit 402 and mixed with a reagent measured by the immunoassay reagent quantification unit 403; and after the assay sample is prepared by the immunosample preparation unit 404, the sample is assayed by the immunosample assay unit 405. In the control unit 5, correction is performed based on the hematocrit stored in the blood analyzer 3 to convert the assay data to antigen concentration or antibody concentration in serum or plasma.

When the blood sample in the container 26 is determined to be unsuited for whole blood immunoassay, the control unit 5 controls the feed unit 10 and the relevant sample container 26 passes through the sample mixing device 42 and sample suction device 43 of the whole blood immunoassay device 4.

Furthermore, the control unit 5 outputs to the output unit 7 the result of the determination as to whether or not the sample is suitable for whole blood immunoassay based on the assay data obtained from the blood analyzer 3 as the table shown in FIG. 15.

When all blood samples suited for whole blood immunoassay have been suctioned from the 10 containers (all sample containers held in one rack 27), the rack 27 is transported in the arrow D direction and collected in the arrow E direction in the rack collection unit 9. When the a rack requiring assay is present on the rack feed unit 8, the rack 27 is transported from the rack feed unit 8 to the rack feed unit 10, and the previously described processing is repeated on the blood samples of each sample container 26 in the rack 27.

In this way in the clinical laboratory test system described above, simply by placing the rack in the system, a determination is made as to whether or not the specimen in the rack is suited for whole blood immunoassay, and at the same time the specimens which are suited for assay can be automatically subjected to whole blood immunoassay and the determination results of specimens which are unsuited for whole blood immunoassay can be displayed. Therefore, until immunoassays of all specimens are completed, an operator need not be constantly in attendance of the system.

In the fourth embodiment, the control unit 5 performs correction based on the hematocrit transmitted from the blood analyzer 3 to convert the assay data to antigen concentration or antibody concentration in serum or plasma; however, the control unit 5 also may perform correction by erythrocyte count assayed by the immunosample assay unit 205 to convert the assay data to antigen concentration or antibody concentration in serum or plasma.

Although the in each of the first through fourth embodiments the whole blood immunoassay apparatus is connected so as to allow communication with a blood analyzer, the whole blood immunoassay apparatus need not necessarily be capable of communication with the blood analyzer inasmuch as assay data obtained by a blood analyzer may be input to the whole blood immunoassay apparatus by an operator. Furthermore, assay data of the blood analyzer may be output on a barcode label, and the assay data may be read from the barcode label adhered to the specimen container by a barcode reader, and input to the whole blood immunoassay apparatus. In this case, the barcode label is desirably a two-dimensional barcode capable of storing a large quantity of information.

In the above embodiments, specimens may be blood or urine normally collected from humans or other animals.

Although the specimen laboratory test apparatus is a whole blood immunoassay apparatus in the above embodiments, other specimen laboratory test apparatus, such as blood coagulation assay apparatus, biochemical analyzer, urine qualitative analyzer, urine sedimentation analyzer and the like, may be used.

Although whether or not a specimen is suited for whole blood immunoassay is determined by the whole blood immunoassay apparatus based on assay data from a blood analyzer in the above embodiments, the determination as to whether or not a specimen is suited for whole blood immunoassay also may be based on attribute information of the patient, including medical history, patient comments, specimen comments and the like.

What is claimed is:

1. A whole blood immunoassay apparatus comprising:
an immunosample analyzing unit configured to immunologically analyze a predetermined marker in a whole blood, the immunosample analyzing unit in communication with a remote blood analyzer including a sample analyzer and a reader configured to generate initial assay data and ID information for a whole blood sample;
a display;
a control unit configured to perform operations comprising:
receiving the initial assay data and the data and the ID information generated by the blood analyzer, wherein the initial assay data includes an erythrocyte count, a hematocrit, a mean erythrocyte volume and a platelet count;
storing threshold values and an anomaly determination equation for each item of the initial assay data in a memory of the control unit and determining an anomaly value for each item of the initial assay data and producing a discrimination result stating whether or not the whole blood sample is suited for analysis by the immunosample analyzing unit based on at least one of the erythrocyte count, the hematocrit, the mean erythrocyte volume or the platelet count;
controlling the immunosample analyzing until to analyze the predetermined marker in the blood sample and to obtain a first analysis result of the predetermined marker when a discrimination result indicates that the blood sample is suited for analysis by the immunosample analyzing unit; and
converting the first analysis result to a second analysis result of the predetermined marker, the second analysis result comprising assay data for serum or plasma based on the hematocrit; and
wherein the blood analyzing transmits the initial assay data over a communications network to the immunosample analyzing unit.

2. The whole blood immunoassay apparatus of claim 1, wherein the operations performed by the control unit further comprise displaying the discrimination result on the display.

3. The whole blood immunoassay apparatus of claim 2, wherein the operations performed by the control unit further comprise displaying an input screen asking whether or not to perform analysis by the immunosample analyzing unit on the display when the discrimination result indicates that the whole blood sample is unsuited for analysis by the analyzing unit.

4. The whole blood immunoassay apparatus of claim 3, wherein the operations performed by the control unit further comprise controlling the immunosample analyzing unit to analyze the predetermined marker in the whole blood and to obtain the second analysis result when an instruction to perform analysis is input on the input screen.

5. The whole blood immunoassay apparatus of claim 1, wherein the control unit receives specimen information from the remote blood analyzer over the communications network.

6. The whole blood immunoassay apparatus of claim 5 further comprising an ID acquisition unit for acquiring ID information for the whole blood sample to be analyzed, wherein the control unit receives the ID information and the specimen information corresponding to the ID information from the blood analyzing apparatus, and determines if the ID information acquired by the ID information acquisition unit and the ID information received by the control unit are matched.

7. The whole blood immunoassay apparatus of claim 6, wherein the control unit discriminates whether or not the whole blood sample is suited for analysis based on received specimen information only when the ID acquired by the ID acquisition unit matches the ID received by the control unit.

8. The whole blood immunoassay apparatus of claim 1, wherein the predetermined marker is a marker for cancer or a marker for an infection.

9. A whole blood immunoassay apparatus comprising:
an immunological analyzing unit programmed to analyze a predetermined marker in a whole blood sample;
a blood analyzing apparatus including a sample analyzer and a reader configured initial assay data and ID information for the whole blood sample, the blood analyzing apparatus remote from the immunological analyzing unit;
a control unit in communication with the immunological analyzing unit and the blood analyzing apparatus, the control unit comprising a processor that executes a computer readable medium comprising a computer program code for:
receiving the initial assay data generated by the blood analyzing apparatus where the initial assay data comprises measurement data that includes an erythrocyte count, a hematocrit, a mean erythrocyle volume and a platelet count;
storing threshold values and an anomaly determination equation for each item of the initial assay data in a memory of the control unit and determining an anomaly value for each of the initial assay data and discriminating whether the whole blood sample is suited for analysis by the immunological analyzing unit based on at least one of the erythrocyte count, the hematocrit, the mean erythrocyte volume or the platelet count;
controlling the immunological analyzing unit to analysis result of the predetermined marker in the whole blood sample and to obtain a first analysis result of the predetermined marker when discrimination result indicates that the whole blood is suited for analysis by the immunological analyzing unit; and
processing the first analysis result to obtain a second analysis result of the predetermined marker, the second analysis result comprising assay data for serum or plasma based on the hematocrit; and
a communications network that transmits the measurement data to the control unit from the blood analyzing apparatus.

10. The whole blood immunoassay apparatus of claim 9 further comprising a network interface and a network server system that transmits the initial assay data and ID information for the whole blood sample from the blood analyzing apparatus to the immunological analyzing unit.

11. The whole blood immunoassay apparatus of claim 9 further comprising an ID acquisition unit for the acquiring ID information, wherein the control unit receives the ID information and specimen information for the whole blood sample corresponding to the ID information from the blood analyzing apparatus, and determines if the ID information acquired by the ID information acquisition unit and the ID information received by the control unit are matched.

12. The whole blood immunoassay apparatus of claim 9 further comprising a communications network and a host computer, wherein the host computer receives the initial assay data and ID information and wherein the host computer includes the control unit.

* * * * *

UNITED STATES PATENT AND TRADEMARK OFFICE
CERTIFICATE OF CORRECTION

| | |
|---|---|
| PATENT NO. | : 8,062,591 B2 |
| APPLICATION NO. | : 10/949099 |
| DATED | : November 22, 2011 |
| INVENTOR(S) | : Norimasa Yamamoto |

It is certified that error appears in the above-identified patent and that said Letters Patent is hereby corrected as shown below:

In the Claims

In column 14, claim 1, line 6, after "initial assay data" delete "and the data".

In column 15, claim 9, line 8, after "a reader configured" insert --to generate--.

In column 15, claim 9, lines 30-31, after "immunological analyzing unit to" replace "analysis result of" with --analyze--.

In column 16, claim 9, line 2, before "discrimination result indicates" insert --a--.

Signed and Sealed this
Third Day of April, 2012

David J. Kappos
*Director of the United States Patent and Trademark Office*